United States Patent [19]

Trugillo

[11] 4,263,921
[45] Apr. 28, 1981

[54] TEMPERATURE SENSING METHOD AND ENDOTRACHEAL TUBE APPLIANCE

[76] Inventor: Katherine H. Trugillo, 1117 Lady Guinevere Dr., Valrico, Fla. 33594

[21] Appl. No.: 679,327

[22] Filed: Apr. 22, 1976

[51] Int. Cl.³ ................. A61M 16/00; A61M 25/00
[52] U.S. Cl. ............................. 128/736; 128/207.14
[58] Field of Search .......... 128/348, 351, 2 H, 2.05 R, 128/207.15, 736

[56] References Cited

U.S. PATENT DOCUMENTS

| 3,081,765 | 3/1963 | Kompelien | 128/2 H |
| 3,499,435 | 3/1970 | Rockwell et al. | 128/351 X |
| 3,862,635 | 1/1975 | Harautuneian | 128/351 |
| 3,951,136 | 4/1976 | Wall | 128/2 H X |
| 4,046,139 | 9/1977 | Horn | 128/736 |

OTHER PUBLICATIONS

Ellenwood et al.-IBM Tech. Disclosure Bulletin-vol. 11, No. 11, Apr. 1969.

*Primary Examiner*—Dalton L. Truluck

*Attorney, Agent, or Firm*—H. Kenneth Johnston, II; Donald W. Margolis

[57] ABSTRACT

A surgical appliance in the form of a temperature sensing endotracheal tube includes any suitable type of endotracheal tube with a temperature sensor in the form of a thermistor mounted on the distal end portion of the tube for engaging the patient's trachea. Suitable wiring is connected with the thermistor and extends through the endotracheal tube side wall to approximately the midpoint of the tube with the free end of the wiring having a suitable connector for attachment to an indicating and/or temperature recording unit. If the distal end portion of the endotracheal tube is provided with a typical inflatable cuff, the thermistor is preferably mounted on the tube proximate the end of the cuff remote from the free end of the distal end portion. The portion of the outer face of the tube which extends across the thermistor preferably protrudes slightly from the adjacent portion of the outer face, to provide better contact with the trachea.

9 Claims, 3 Drawing Figures

TEMPERATURE SENSING METHOD AND ENDOTRACHEAL TUBE APPLIANCE

This invention relates to a surgical appliance and, more particularly, to a temperature sensing endotracheal tube unit.

BACKGROUND OF THE INVENTION

During surgery a patient's temperature is normally monitored as by a rectal probe or a probe inserted into an ear cavity, the probe often being in the form of a thermistor wired to appropriate temperature indicating and/or recording equipment. The anesthetist, having primary concern with monitoring and maintaining vital functions of the patient during surgery, is of course concerned with any changes in the patient's temperature. While rectal and ear temperature sensors normally function properly during an operation, they may become unseated and fail to correctly sense the patient's temperature, and when this occurs the sensor must be reseated by a nurse or other attendant as the anesthetist is otherwise occupied with administering the anesthetic and oxygen. Additionally, rectal and ear probes may cause discomfort to the patient and irritation which may continue to cause discomfort after the patient has come out of the anesthetic, resulting in increased trauma. Finally, rectal, ear, and other types of temperature sensors add to the amount of equipment needed during surgery, and tend to further complicate the procedures.

By combining a temperature sensor with a typical endotracheal tube more reliable monitoring of the patient's temperature may be obtained during surgery, in part because the person immediately concerned with monitoring the patient's vital signs, the anesthetist, has the temperature sensor under his immediate control and is constantly at hand to make necessary adjustments in the equipment during the surgery. Fewer pieces of equipment are necessary when the temperature sensor is combined with the endotracheal tube than when a rectal or ear sensor must be provided in addition to the endotracheal tube, and since fewer portions of the patient's body are affected by use of the combined temperature sensor and endotracheal tube unit than with the other types of sensors, there is less likelihood of a traumatic reaction by the patient.

The following United States patents are known to applicant, and while not particularly pertinent to the present invention are called to the examiner's attention: U.S. Pat. Nos. 3,081,765; 3,499,435, and 3,734,094. The first of these patents shows a rectal probe for monitoring a patient's breathing and temperature and utilizes a thermistor. U.S. Pat. No. 3,499,435, shows an "Esophageal Probe For Use In Monitoring" and incorporates a tube for withdrawing stomach fluids and in addition to other features incorporates a temperature probe. The last of these patents is also directed to an esophageal instrument and is provided with electrode bands encircling the tube for monitoring heart functions.

BRIEF STATEMENT OF THE INVENTION

The invention, in brief, is directed to a surgical appliance having a temperature sensor combined with an endotracheal tube. The sensor is preferably mounted on the distal end portion of the endotracheal tube in position to contact the mucous membrane of the trachea or oropharynx, for monitoring the patient's temperature during surgery. In the preferred embodiment a thermistor serves as the temperature sensor and is connected by wiring with suitable temperature monitoring and/or recording equipment. Both the thermistor and a portion of the wiring extend longitudinally about half the length of the endotracheal tube within the inner and outer faces of the tube side wall, the portion of the outer face which extends across the thermistor being preferably bulged out slightly for better contact with the mucous membrane. If the endotracheal tube is provided with a typical inflatable cuff, the thermistor is preferably located closely proximate the end of the cuff remote from the distal free end of the endotracheal tube.

In the illustrated embodiment the endotracheal tube may be of any suitable type and is illustrated as provided with an annular inflatable cuff about the distal end portion of the tube, but sometimes the tubes are provided without a cuff particularly for use on small children. In any event, the temperature sensor is mounted at the distal end portion of the endotracheal tube and when a cuff is provided the sensor is preferably located between the cuff and the proximal end connector of the tube. The temperature sensor is illustrated in the form of a thermistor embedded within the wall of the tube, the outer face of the wall which extends across the thermistor being bulged slightly outwardly for better contact with the mucous membrane of the patient's trachea or oropharynx, therefore monitoring a constant body core temperature. Suitable wiring extends longitudinally through the tube side wall and connects the thermistor with a suitable connection for temperature monitoring and/or recording equipment. By mounting the thermistor within the side wall of the tube, and preferably proximate the outer face of the side wall and remote from the inner face of the side wall, more accurate sensing of the patient's temperature rather than the temperature of the gases passing through the hollow of the tube is obtained. Obviously, if the thermistor and its wiring is simply passed through the hollow of the tube and through the opening at its distal end, hopefully for contact with a portion of the patient's trachea, the thermistor is quite likely to sense the temperature of the gases passing through the tube rather than accurately sensing the patient's temperature.

It is a primary object of this invention to provide a new and useful surgical appliance and, more particularly, provision of such an appliance in the form of a temperature sensing endotracheal tube.

Another object is provision of a new and useful surgical appliance for sensing a patient's temperature during surgery and incorporating an existing appliance used during surgery so that no additional patient contacting equipment is necessitated for the temperature sensing function. A related object is provision of such an appliance which eliminates the need for disturbing additional portions of the patient's body in order to sense the patient's temperature, thus eliminating the possibility of additional discomfort and possible trauma.

Still another object is provision of a new and useful surgical appliance for sensing a patient's temperature, the appliance being under the immediate control of the anesthetist.

A still further object is provision of a new and useful surgical appliance in which a temperature sensor is incorporated in an economical and reliable manner into a typical endotracheal tube.

A more specific object is provision of a new and useful surgical appliance including an endotracheal tube having a distal end portion for normal receipt during surgery within a patient's trachea, with provision for determining the patient's temperature and including a temperature sensor mounted on the tube. A related object is provision of the sensor at the distal end portion of the tube. Another related object is provision for transmitting a signal responsive to the temperature sensed by the sensor and, more particularly, the sensor being in the form of a thermistor and the signal being transmitted by electric wires connected therewith and extending longitudinally within the tube side wall toward its proximal end and, more particularly, the outer face of the tube wall being generally cylindrical and a portion thereof which extends across the thermistor protruding outwardly from the adjacent portion of the outer face. A still further related object is provision of a typical inflatable cuff at the distal end portion of the endotracheal tube, and the thermistor being proximate an end of the cuff remote from the free end of the distal end portion of the tube.

These and other objects and advantages of the invention will be apparent from the following description and the accompanying drawing.

DESCRIPTION OF THE ILLUSTRATED EMBODIMENT

Figure 1:
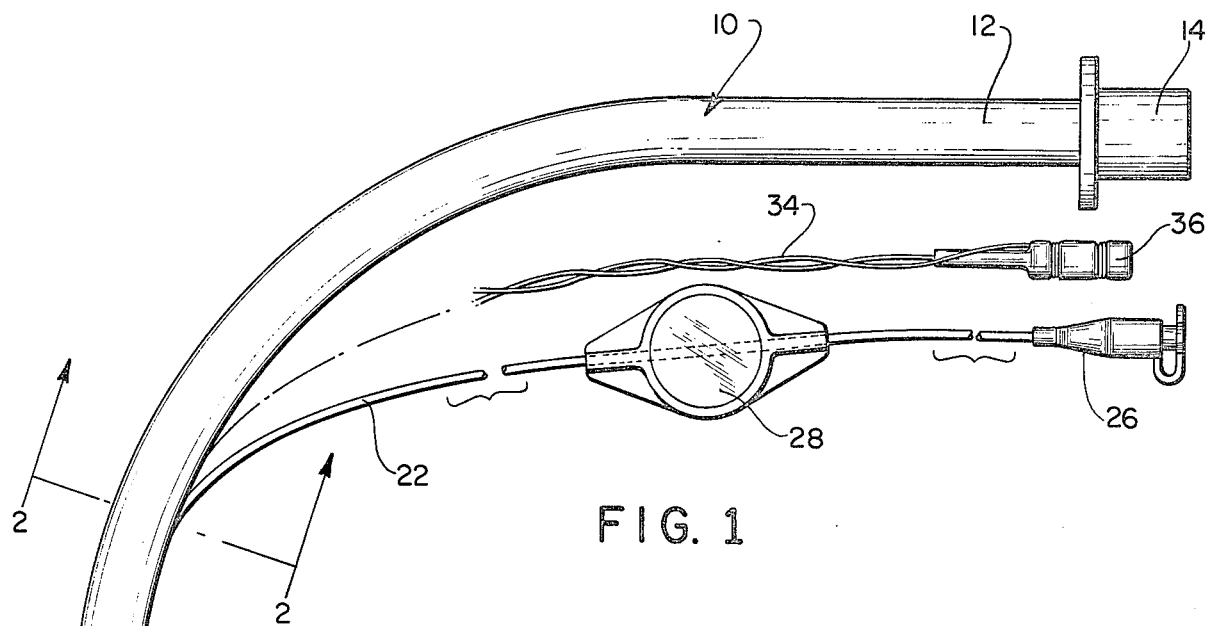
FIG. 1 is a schematic, side view of a preferred embodiment of a surgical appliance in the form of an endotracheal tube and temperature sensing unit with portions of the appliance foreshortened.
Figure 2:
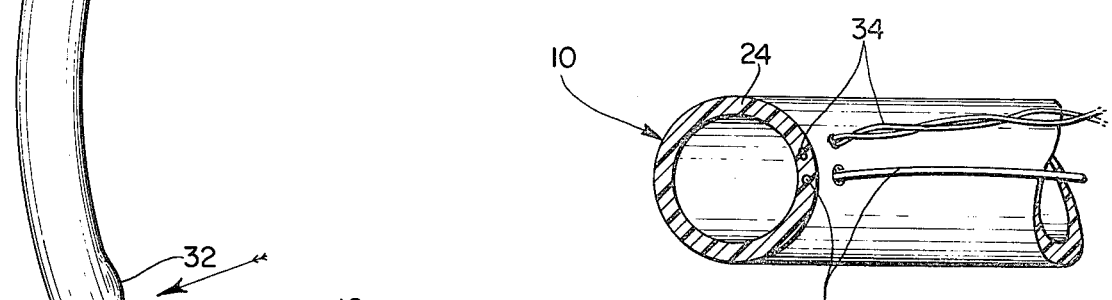
FIG. 2 is an enlarged, sectional view taken generally along the line 2—2 in FIG. 1.

Referring first to FIG. 1 of the drawing, a surgical appliance in the form of an endotracheal tube and temperature sensing unit may utilize any suitable type of endotracheal tube 10. Such tubes have a proximal end 12 normally telescopically receiving the usual endotracheal tube connector 14, with a distal end portion 16 including the typical bevel 18 and elongated hole 20. While not provided on all such tubes, but as shown in the illustrated embodiment, the distal end portion 16 further includes a typical inflatable cuff 21 which receives inflating air through a tube 22 passing within the wall 24 (FIGS. 2 and 3) of the endotracheal tube 10 and extending from the wall 24 to a connection shown in the form of an air lock 26 and an intermediate portion of the air tube 22 being provided with a typical air check bag 28. The endotracheal tube 10 is preferably generally cylindrical in cross-section throughout its length, including the portion of the wall 24 through which the air tube 22 extends.

Figure 3:
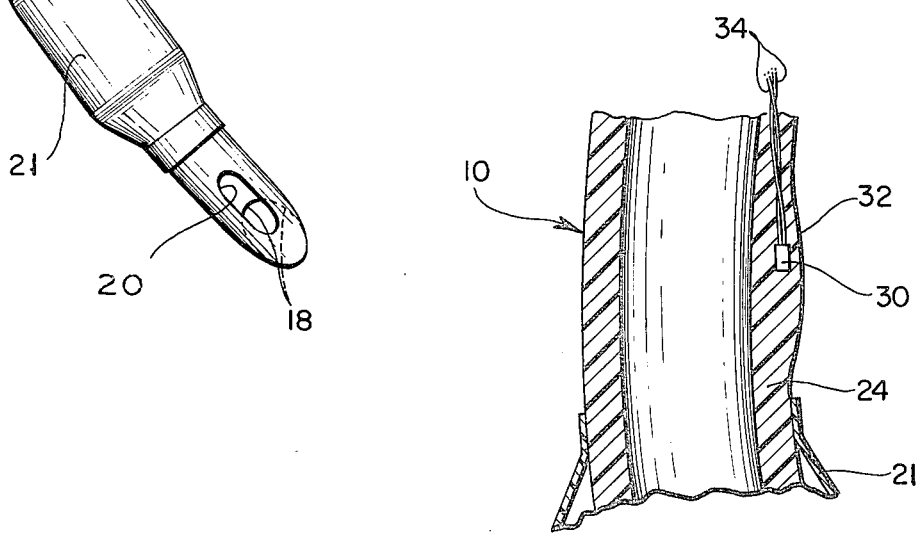
FIG. 3 is a further enlarged, diametrical sectional view taken generally parallel to the plane of the drawing sheet, and illustrating a portion of the unit indicated generally by the arrow in FIG. 1.

In order to conveniently and reliably determine the patient's temperature during surgery, a temperature sensing device, which may be of any suitable form, and preferably, as illustrated, is an electrical sensor in the form of a thermo-couple or thermistor 30, for example, and is provided at the distal end portion 16 of the endotracheal tube 10. Thermistor 30 is preferably above the inflatable cuff 21 and is embedded in the side wall 24 of the endotracheal tube 10 preferably close to its outer face. As illustrated in FIGS. 1 and 3, the outer face of the endotracheal tube 10 is preferably provided with a slight bulge 32 adjacent the thermistor 30 for better contact with the mucous membrane of the posterior pharynx or trachea. A pair of lead wires 34 extend from the thermistor 30 and through the endotracheal tube side wall 24. These wires 34 are preferably molded within the side wall in a manner similar to the air inflating tube 22, and exit from the side wall 24 proximate the exit point of the air tube 22. The proximal or outer ends of the lead wires terminate in a suitable connector 36 for connection with suitable temperature indicating and/or recording equipment (not shown).

While this invention has been described and illustrated with reference to a particular embodiment in a particular environment, various changes may be apparent to one skilled in the art and the invention is therefore not to be limited to such embodiment or environment except as set forth in the appended claims.

What is claimed is:

1. A combined temperature sensing and endotracheal medical appliance including, in combination:

a tube, said tube being defined by side walls, said side walls being generally cylindrical in cross-section and having an inner surface and an outer surface, the diameter across the outer surface being somewhat smaller than the opening of the human trachea, said tube terminating in an open proximal end and in an opposed open distal end, said distal end being smooth and beveled, and the body of said tube longitudinally between said proximal and distal ends normally being in the form of a gentle curve replicating the curvature of the human trachea; a protuberance on said outer surface of said tube, said protuberance being proximate to, but spaced from, said distal end of said tube;

means for sensing temperature, said temperature sensing means being carried within said protuberance in temperature sensing relationship with the environment external to said appliance and substantially thermally insulated from the environment within said tube and the environment at the distal end of said tube, whereby said distal end of said tube may be smoothly inserted into a patient's trachea in a manner to permit respiration to continue and/or an inhalant to pass through said tube, while said protuberance carried by said tube is in contact with the mucous membranes of the trachea or oropharynx, to simultaneously sense the patient's temperature.

2. The appliance of claim 1 wherein means for transmitting temperature information from said appliance is operatively connected to said temperature sensing means.

3. The appliance of claim 2 wherein said information transmitting means is means for transmitting electrical currents.

4. The appliance of claim 3 wherein said electric current transmitting means is electric wiring, said wiring being carried longitudinally within at least a portion of said tube side wall from said temperature sensing means towards said proximal end.

5. The appliance of claim 4 wherein said wiring terminates in a connection suitable for use with temperature monitoring equipment.

6. The appliance of claim 5 wherein said wiring terminates in a connection suitable for use with temperature recording equipment.

7. The appliance of claim 4 wherein said wiring extends longitudinally within said side wall from said temperature sensing means approximately half the length of said tube, and thence continues externally of the tube.

8. The appliance of claim 4 wherein said temperature sensing means is a thermistor.

9. The method of allowing respiration to continue and/or an inhalant to be passed to a patient's trachea while simultaneously sensing the temperature of said patient's trachea or oropharynx comprising the steps of:

inserting the distal end of the appliance of claim 11 within a patient's trachea with the curve of said tube oriented to conform to the curve of the trachea and in a manner to permit respiration to continue and/or an inhalant to be administered through said tube;

contacting the mucous membrane of the patient's trachea or oropharynx with said protuberance on said appliance; and then allowing an inhalant into the proximal end of said tube, and through said tube to exit the open distal end of said tube.

* * * * *